United States Patent
Georgiou

(10) Patent No.: US 10,905,671 B2
(45) Date of Patent: Feb. 2, 2021

(54) METHOD OF USING OMEGA 3 FATTY ACIDS TO TREAT DISEASES WHICH INVOLVE DAMAGE TO THE NERVOUS SYSTEM

(71) Applicant: Tassos Georgiou, Nicosia (CY)

(72) Inventor: Tassos Georgiou, Nicosia (CY)

( * ) Notice: Subject to any disclaimer, the term of this patent is extended or adjusted under 35 U.S.C. 154(b) by 0 days.

(21) Appl. No.: 15/977,354

(22) Filed: May 11, 2018

(65) Prior Publication Data

US 2019/0192466 A1 Jun. 27, 2019

Related U.S. Application Data

(63) Continuation-in-part of application No. 15/106,475, filed as application No. PCT/EP2013/077356 on Dec. 19, 2013, now abandoned.

(51) Int. Cl.
*A61K 31/202* (2006.01)
*A61P 25/00* (2006.01)
*A61P 27/06* (2006.01)
*A23L 33/12* (2016.01)

(52) U.S. Cl.
CPC ............ *A61K 31/202* (2013.01); *A23L 33/12* (2016.08); *A61P 25/00* (2018.01); *A61P 27/06* (2018.01); *A23V 2002/00* (2013.01)

(58) Field of Classification Search
CPC ........ A61K 31/202; A61P 25/00; A61P 27/06; A23L 33/12
See application file for complete search history.

(56) References Cited

U.S. PATENT DOCUMENTS

| | | |
|---|---|---|
| 2010/0254951 A1 | 10/2010 | Shido |
| 2011/0237547 A1 | 9/2011 | Minatelli et al. |
| 2012/0053242 A1 | 3/2012 | Lopez et al. |

FOREIGN PATENT DOCUMENTS

| | | |
|---|---|---|
| WO | WO2012/112340 | 8/2012 |
| WO | WO20120103049 | 8/2012 |
| WO | WO2012125020 | 9/2012 |

OTHER PUBLICATIONS

Nyborg N C B et al, "Reduced Intraocular Pressure in Healthy Volunteers After Dietary Supplementation with Fish Oil (Pikasol): A double Blind Study", IOVS, vol. 39, No. 4, Mar. 15, 1998, p. S441 and Annual Meeting of the Association for Research in Vision and Ophthalmology: Ft. Lauderdale, FL, USA, May 10-15, 1998.
Barry Sears, et al.: "Therapeutic uses of high-dose omega-3 fatty acids to treat comatose patients with severe brain injury", Pharmanutrition, vol. 1, No. 3, Jul. 1, 2013, pp. 86-89.
Gandolfo E et al.: "The effect of an association of docosahexaenoic acid and B vitamins complex on initial visual field damage in primary open angle glaucoma", IOVS, vol. 39, No. 4, Mar. 15, 1998, p. S261 and Annual Meeting of the Association for Research in Vision and Ophthalmology: Ft. Lauderdale, FL, USA, May 10-15, 1998.

*Primary Examiner* — Zohreh A Fay
(74) *Attorney, Agent, or Firm* — Bay State IP, LLC

(57) ABSTRACT

Method of administering compositions comprising omega 3 fatty acids for use in the treatment, amelioration or prevention of various conditions, disorders, and diseases which involve damage to the nervous system.

6 Claims, 11 Drawing Sheets

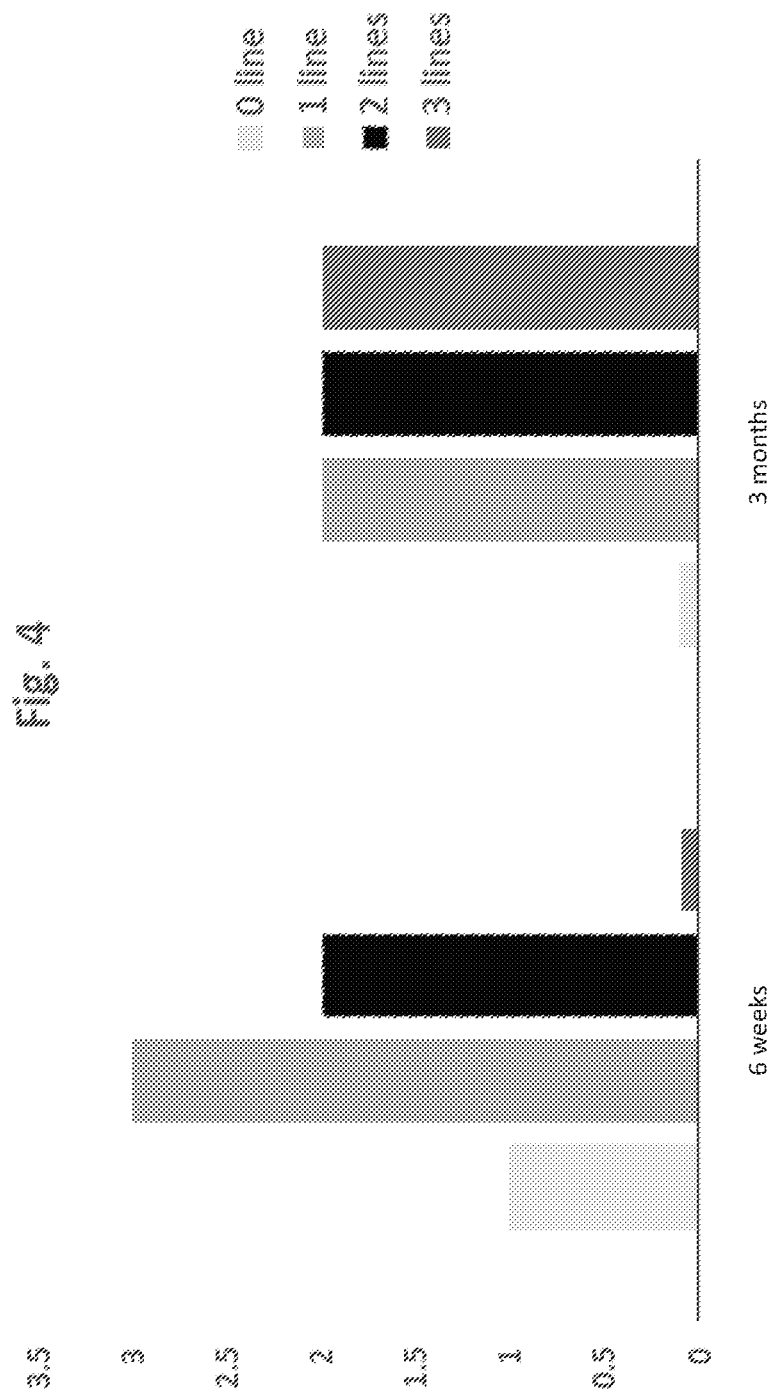

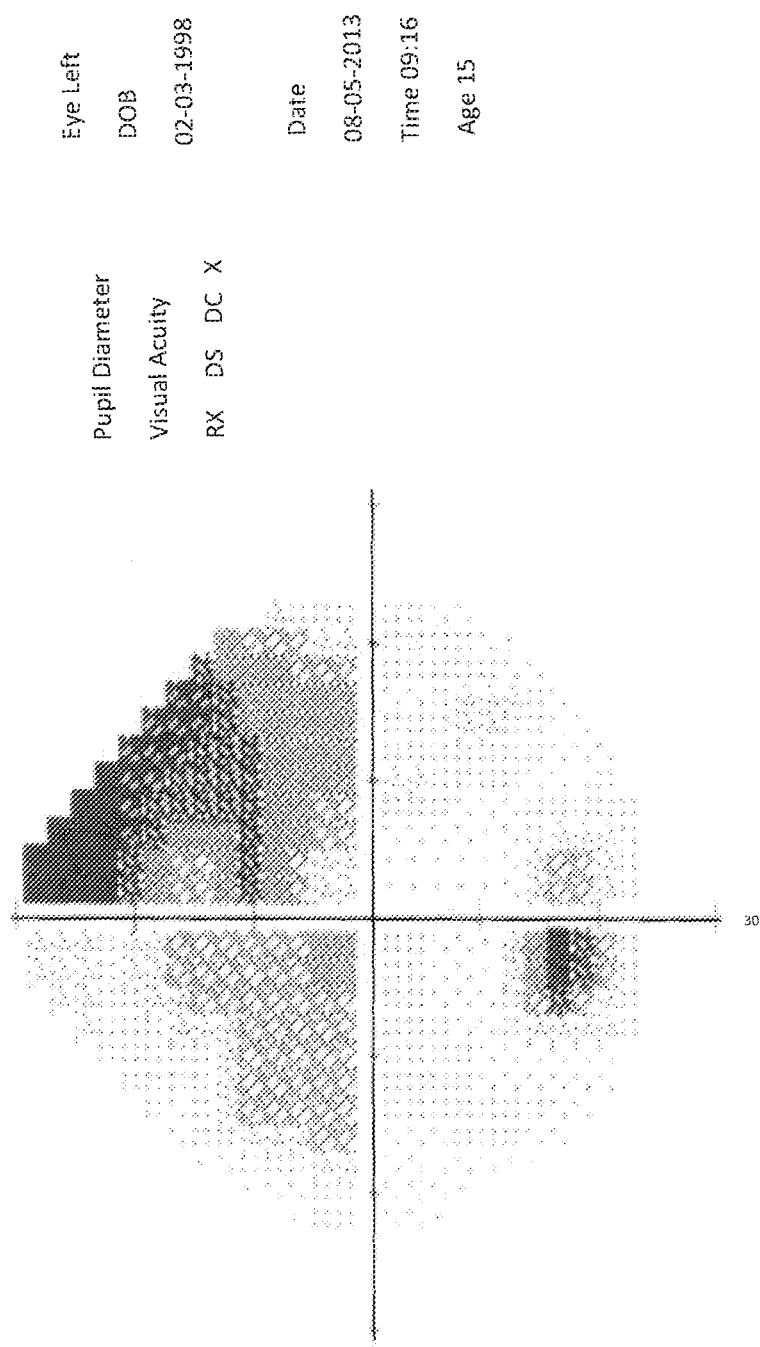

METHOD OF USING OMEGA 3 FATTY ACIDS TO TREAT DISEASES WHICH INVOLVE DAMAGE TO THE NERVOUS SYSTEM

FIELD OF THE INVENTION

The present invention relates generally to the fields of medicine, foods, and health food supplements. More particularly, it relates to methods of using compositions of omega 3 fatty acids for use in the treatment of a disease, and in particular to methods of using compositions comprising eicosapentaenoic acid (EPA) and docosahexaenoic acid (DHA) for use in the treatment, amelioration or prevention of various conditions, disorders, and diseases which involve damage to the nervous system, as the peripheral nervous system neuropathy and glaucoma.

BACKGROUND OF THE INVENTION

Neuropathy is damage or disease involving nerves, which may affect sensation, movement, gland or organ function and other aspects of health, depending on the type of nerve affected. Common causes include systemic diseases (such as diabetes or leprosy), vitamin deficiency, medication (e.g., chemotherapy), traumatic injury, excessive alcohol consumption, immune system disease or infection, or it may be inherited (present from birth).

Peripheral neuropathy (PN) is damage or disease involving nerves, which may affect sensation, movement, gland or organ function and other aspects of health, depending on the type of nerve affected. Common causes include systemic diseases (such as diabetes or leprosy), vitamin deficiency, medication (e.g., chemotherapy), traumatic injury, excessive alcohol consumption, immune system disease or infection, or it may be inherited (present from birth).

The prevalence of peripheral neuropathy in the family medicine setting is 8 percent in persons 55 years and older. (Martyn & Hughes 1997. J Neurol Neurosurg Psychiatry. 62(4):310-318). The prevalence in the general population may be as high as 2.4 percent (Hughes 2002. BMJ. 324 (7335):466-469). A community-based study estimated the prevalence of peripheral neuropathy in patients with type 2 diabetes mellitus to be 26.4 percent (Davies et al., 2006. Diabetes Care. 29(7):1518-1522).

The peripheral nervous system (PNS, or occasionally PeNS) is the part of the nervous system consisting of the nerves and ganglia outside of the brain and spinal cord. The cranial nerves are part of the PNS with the exception of cranial nerve II, the optic nerve, along with the retina. The second cranial nerve is not a true peripheral nerve but a tract of the diencephalon. Cranial nerve ganglia originate in the CNS. However, the remaining eleven cranial nerve axons extend beyond the brain and are therefore considered part of the PNS.

Facial neuropathy produces weakness of the muscles of facial expression and eye closure. Voluntary eye closure may not be possible and can result in damage to the cornea and conjunctiva.

Eye movements are subserved by the ocular motor nerves (cranial nerves 3, 4 and 6) which innervate the 6 muscles of each eye. The oculomotor (3rd) nerve innervates the medial rectus, inferior rectus, superior rectus and inferior oblique as well as the levator palpebrae. The trochlear (4th) nerve innervates the superior oblique muscle and the abducens (6th) nerve innervates the lateral rectus muscle. Facial and ocular motor nerves neuropathies can be due to ischaemia, inflammation and/or trauma. There is no current treatment for these eye pathologies.

Conditions like scleritis, thyroid eye disease, chronic uveitis and keratoconjunctivitis are due to inflammation. Current treatments include steroids and immunosuppressive agents. Conjunctival and corneal wounds can be due to inflammation or due to decreased sensation of the nerve supplies. There is a need for more effective and/or alternative therapies for treating the above conditions.

Optic nerve damage can occur mainly due to glaucoma, ischaemia, inflammation or trauma. Currently there is no treatment to limit axonal injury and improve neuronal function in these patients.

Glaucoma is the second leading cause of blindness worldwide, effecting 80 million people with approximately 7 million people blind. It affects 1-2% of the US population. Glaucoma consists of a group of disorders that lead to retinal ganglion cell death. In most forms of glaucoma elevated intraocular pressure is considered the single most important factor for developing glaucoma. However, high intraocular pressure is not present in some forms of glaucoma like Normal Tension Glaucoma. Glaucoma is characterized by progressive damage to the optic nerve, accompanied by gradual loss of the visual field, starting at the periphery and extending to the center. It may or may not be directly related to the level of intraocular pressure.

Glaucoma can be divided into 3 main groups: (1) Open angle glaucoma, which is subdivided into high pressure glaucoma (primary open angle glaucoma), and normal pressure glaucoma (normal tension glaucoma); (2) Closed angle glaucoma; (3) Secondary glaucoma.

In glaucoma there is a breakdown of blood-retina barrier. This results in an inflammatory response and damage to retinal ganglion cells by vascular dysregulation resulting in periods of ischaemia and reperfusion damage. As a result of ischaemia there is elevation of inflammatory cytokines and chemokines such as VEGF, TNF-a, IL, CRP, NO etc. Ischaemia also causes an increase of endothelin-1 which is a vasoconstrictive, thus promoting hypoxia and ischaemia which result in retinal ganglion cell death.

Glaucoma is a chronic disease and the current mainstay of therapy is aimed at lowering intraocular pressure to slow disease progression. Medication in terms of eye drops is the usually accepted first line treatment followed by laser treatment and incisional surgery. The goal of therapy is to reduce the intraocular pressure by at least 20% given the results of OHTS, AGIS and the EMGT studies which showed reduction of at least 40% of rates of worsening of field testing versus no treatment. There is a higher risk of field loss among patients who have larger intraocular pressure swings at different times of the day.

Late diagnosis or advanced visual field loss at the time of diagnosis are among the primary risk factors for progression to blindness in glaucoma. It has been estimated that late presentation is the main cause of blindness in one-third of glaucoma patients who become blind.

With a growing aging population, there is an increase of glaucoma blindness in the world. By understanding glaucoma pathophysiology we can better improve our treatments to improve care for our glaucoma patients.

60% of glaucoma patients suffer from dry eye disease which can reduce quality of life and compliance of glaucoma treatment. Multiple daily exposures of the ocular surface to active compounds and preservatives can worsen the burden of dry eye disease in this population.

Glaucoma research has seen an increasing focus on neuroprotection. Even a small benefit in patients with advanced glaucoma damage with reduced vision would be beneficial.

Degeneration of retinal ganglion cells has been observed in diseases of the nervous system such as Parkinson's disease and Alzheimer's without glaucoma. Inflammation plays a role in these nervous system diseases which also causes the damage to the retinal ganglion cells.

During the last twenty (20) years, controlled clinical trials showed that lowering intraocular pressure can slow glaucoma progression. Any new treatment should have a neuroprotective effect to reduce the remaining progression rate below that achieved by intraocular pressure-based therapy alone. The neuroprotective treatment must have minimal visual or systemic side effects otherwise it will not be tolerated by patients.

Intraocular pressure lowering therapy slows the untreated rate of progression by about 50%. Therefore the aim of neuroprotection is to reduce the progression by another 50%.

Ischaemic Optic Neuropathy (ION) secondary to vasculitis. Non arteritic anterior ischaemic optic neuropathy (NAION) is the most common cause of acute optic neuropathy in patients over the age of 50 years old. It affects up to 10 people per 100000. Symptoms include acute unilateral painless of vision. Any region in the visual field can be affected. More than 50% of patients with ION are blind (<20/200 vision) with constricted visual fields.

The mechanism of ischaemia remains unknown. Studies have shown that hypertension (47%-49%) and diabetes (24%-26%) were present in NAION. Sleep apnea, hypoperfusion, severe anemia and nocturnal hypotension are all potential but unproven risk factors for NAION.

In most cases of ischaemic optic neuropathy vision worsens progressively over two weeks and then remains stable over time. The risk for the fellow eye is 15% within 5 years. Visual acuity appears to plateau round the time that disk oedema is superseded by optic atrophy.

Currently there is no generally accepted treatment for ischaemic optic neuropathy. Systemic steroids have been used to try to decrease capillaries permeability and resolve the oedema faster. This would reduce compression of capillaries and improve the blood flow. In one study patients given oral steroids had resolution of oedema in 6.8 weeks compared to 8.2 weeks in untreated cases. Visual fields and vision can improve up to maximum of 6 months but not thereafter. Intravitreal tramcinolone and intravitreal VEGF have been used and reported as case reports. Optic neuritis Optic neuritis is an acute inflammatory demyelinating disorder of the optic nerve that occurs most often in young adults and can be associated with multiple sclerosis. Even though good functional vision recovery is seen in most patients, some patients fail to recover (5-10%). Optic neuritis is the initial presentation of multiple sclerosis in up to 20% of patients. Ophthalmologists are usually the first doctors to see patients with multiple sclerosis related visual symptoms. It is an autoimmune disease with perivascular infiltration of immune cells across the blood brain barrier. These immune cells destroy the myelin and cause demyelination. Inflammatory cellular and humoral immune mechanisms play a major role in optic neuritis.

The optic neuritis treatment trial showed that 3 days of intravenous methylprednisolone hastens visual recovery, although many patients recover vision regardless. Low dose oral steroids have shown to increase the chance for recurrent optic neuritis and the reason is unclear.

Conditions like scleritis, thyroid eye disease, chronic uveitis and keratoconjunctivitis are due to inflammation. Current treatments include steroids and immunosuppressive agents.

Conjunctival and corneal wounds can be due to inflammation or due to decreased sensation of the nerve supplies.

In summary, there is a need for more effective and/or alternative therapies for treating the above conditions.

The methods described in this patent represent a novel therapeutic approach to reduce morbidity resulting from diseases which involve damage to the nervous system, and particularly for use in treatment of 2nd cranial (optic) nerve neuropathy, 3rd cranial nerve neuropathy (occulomotor), 4th cranial nerve neuropathy (trochlear), 6th cranial nerve neuropathy (abducent), 7th nerve neuropathy (facial), optic nerve damage, and other eye pathologies due to inflammation.

SUMMARY OF THE INVENTION

The present invention provides novel methods of administering compositions comprising omega 3 fatty acid for use in the treatment, amelioration or prevention of various conditions, disorders, and diseases which involve damage to the nervous system, as the peripheral nervous system neuropathy and glaucoma.

Thus, a first aspect of the present invention refers to a method of administering a composition comprising at least 3 g of omega 3 fatty acids. In a preferred embodiment of the first aspect of the invention, the method comprises administering a composition comprising at least 3.4 g of omega 3 fatty acids, and more preferably, at least 5 g of omega 3 fatty acids.

In another preferred embodiment of the first aspect of the invention, the method includes administering a composition comprising from 5 g to 15 g of omega 3 fatty acids.

In another preferred embodiment of the first aspect of the invention, the omega 3 fatty acid is selected from the list consisting of: eicosapentaenoic acid (EPA), docosahexaenoic acid (DHA), alpha liniolenic acid (ALA), stearidonic acid (SA), oeicosatetraenoic acid, or any combination thereof. In a more preferred embodiment of the first aspect of the invention, the omega 3 fatty acid is eicosapentaenoic acid (EPA).

In a further preferred embodiment of the first aspect of the invention, the omega 3 fatty acids are a combination of eicosapentaenoic acid (EPA) and docosahexaenoic acid (DHA). In a still further preferred embodiment of the first aspect of the invention, eicosapentaenoic acid (EPA) and docosahexaenoic acid (DHA) are in a mass ratio from 1:1 to 5:1. Still more preferably, the eicosapentaenoic acid (EPA) and docosahexaenoic acid (DHA) are in a mass ratio of about 2:1.

In a still further preferred embodiment of the first aspect of the invention, said composition administered is a pharmaceutical composition which optionally comprises an acceptable pharmaceutical carrier and/or additional active ingredients. More preferably, the pharmaceutical composition comprises at least 50% weight omega 3 fatty acids.

In another preferred embodiment, the composition administered is an oral dosage form. More preferably the oral dosage form is selected from the group comprising tablets, capsules, caplets, slurries, sachets, suspensions, chewing gum, and powder formulation that may be dissolved in a liquid. In a still more preferable embodiment, the oral dosage form is a suspension. In another still more preferable embodiment, the oral dosage form is a powder.

In another preferred embodiment, the composition administered is a food composition or a health food supplement. More preferably, the food composition comprises at least 50% weight omega 3 fatty acids.

A second aspect of the invention refers to a kit of parts comprising eicosapentaenoic acid (EPA) and docosahexaenoic acid (DHA) in a mass ratio from 1:1 to 5:1.

In a preferred embodiment of the second aspect of the invention, the eicosapentaenoic acid (EPA) and docosahexaenoic acid (DHA) are a mass ratio of about 2:1.

In a still further preferred embodiment of the second aspect of the invention, said kit of parts is a pharmaceutical kit of parts which optionally comprises an acceptable pharmaceutical carrier and/or additional active ingredients. More preferably, the additional active ingredient is a steroid, an anti-drug or a nutritional supplement.

In another embodiment of the first aspect of the invention, said kit of parts that is administered is a food composition.

A third aspect of the inventions refers to the administration of the composition or the kit of parts of the invention for use in therapy or for use as a medicament.

A fourth aspect of the invention refers to the administration of the composition or the kit of parts of the invention, for its use in the treatment, amelioration or prevention of diseases which involve damage to the nervous system, as the peripheral nervous system neuropathy and glaucoma.

In a preferred embodiment of the fourth aspect of the invention, the diseases which involve damage to the nervous system is selected from the group consisting of 2nd cranial (optic) nerve neuropathy, 3rd cranial nerve neuropathy (oculomotor), 4th cranial nerve neuropathy (trochlear), 6th cranial nerve neuropathy (abducent), 7th nerve neuropathy (facial), optic nerve damage, and other eye pathologies due to inflammation.

Optic nerve damage can occur mainly due to glaucoma, ischaemia, inflammation or trauma.

In a more preferred embodiment of the fourth aspect of the invention, the optic nerve damage is selected from the group consisting of optic nerve damage due to glaucoma, ischaemic optic neuropathy (ION), and optic neuritis, or any combination thereof. In another preferred embodiment of the fifth aspect of the invention, the eye pathology due to inflammation is selected from the group consisting of scleritis, thyroid eye disease, chronic uveitis, vernal and atopic keratoconjunctivitis, conjunctival and corneal wounds. A particular embodiment of the fourth aspect of the invention refers to administering the composition or the kit of parts for its use in the treatment, amelioration or prevention of glaucoma.

In a more preferred embodiment, the pharmaceutical composition or kit of parts can be administered one or more times a day; for example, 1, 2, 3 or 4 times a day, in a typical total daily amount to be above 5 g per day of omega 3 fatty acids, more preferably to be above 5 g per day of eicosapentaenoic acid (EPA) and docosahexaenoic acid (DHA), and more preferably comprised between 5 g to 15 g per day. Preferably, the combined dosage is from 7.5 g to 10 g per day. In a more preferred embodiment, the pharmaceutical composition or kit of parts can be administered in a dose wherein the combined EPA and DHA is such that the arachidonic acid/eicosapentaenoic acid mass ratio in the blood is in the range of 0.8 to 3 preferably from 1 to 1.5.

A fifth aspect of the invention refers to the administration of the food composition of the invention, for the treatment, amelioration or prevention of diseases which involve damage to the nervous system, as the peripheral nervous system neuropathy and glaucoma.

In a preferred embodiment of the fifth aspect of the invention, the diseases which involve damage to the nervous system is selected from the group consisting of 2nd cranial (optic) nerve neuropathy, 3rd cranial nerve neuropathy (oculomotor), 4th cranial nerve neuropathy (trochlear), 6th cranial nerve neuropathy (abducent), 7th nerve neuropathy (facial), optic nerve damage, and other eye pathologies due to inflammation.

Optic nerve damage can occur mainly due to glaucoma, ischaemia, inflammation or trauma.

In a more preferred embodiment of the fifth aspect of the invention, the optic nerve damage is selected from the group consisting of optic nerve damage due to glaucoma, ischaemic optic neuropathy (ION), and optic neuritis, or any combination thereof. In another preferred embodiment of the fifth aspect of the invention, the eye pathology due to inflammation is selected from the group consisting of scleritis, thyroid eye disease, chronic uveitis, vernal and atopic keratoconjunctivitis, conjunctival and corneal wounds. A particular embodiment of the fifth aspect of the invention refers to the administration of the food composition of the invention for the treatment, amelioration or prevention of glaucoma. More preferably, the composition or the kit of parts of the invention is administered to a patient population that is poorly responsive or nonresponsive to steroids.

In a more preferred embodiment, the food composition of the invention can be administered one or more times a day; for example, 1, 2, 3 or 4 times a day, in a typical total daily amount to be above 5 g per day of omega 3 fatty acids, more preferably to be above 5 g per day of eicosapentaenoic acid (EPA) and docosahexaenoic acid (DHA), and more preferably comprised between 5 g to 15 g per day. Preferably, the combined dosage is from 7.5 g to 10 g per day. In a more preferred embodiment, the pharmaceutical composition or kit of parts of the invention can be administered in a dose wherein the combined EPA and DHA is such that the arachidonic acid/eicosapentaenoic acid mass ratio in the blood is in the range of 0.8 to 3 preferably between 1 to 1.5.

BRIEF DESCRIPTION OF THE DRAWINGS

A complete understanding of the present invention may be obtained by reference to the accompanying drawings, when considered in conjunction with the subsequent detailed description, in which:

FIG. 4 shows the number of lines gained and the number of eyes over the period of 4.5 months in the example 2. There is an increase of 1.6 lines of visual acuity at 6 weeks, 2.4 lines at 3 months and 2.5 lines at 4.5 months. There was also improved visual field testing in all the cases that were tested. Average lines gained at 3 months is 2.

FIGS. 6A-6C show an example of a 15 year old boy who presented 14 months following a road traffic accident. His visual acuity was 20/40 and had optic nerve damage as shown with the field test. He was started on 7.5 g per day of the composition of the invention. 5.5 months following treatment his visual acuity improved by 2.5 lines and the field test has improved as shown.

DETAILED DESCRIPTION OF THE PREFERRED EMBODIMENT

Figure 1:
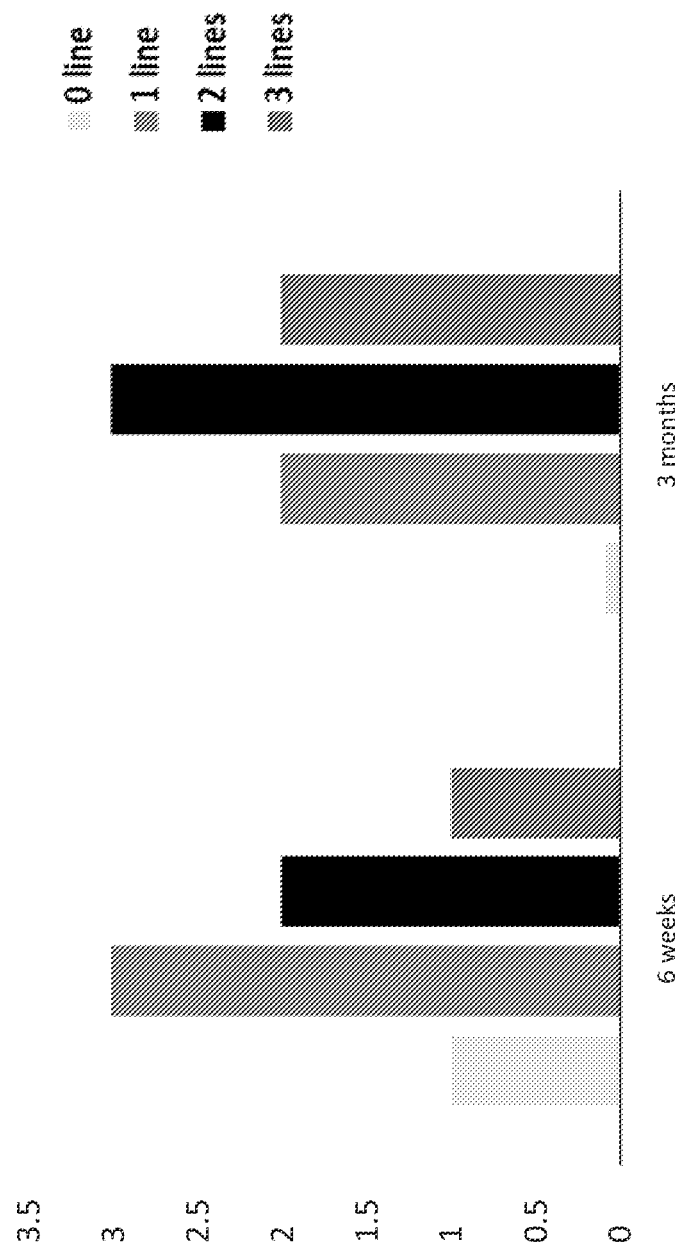
FIG. 1 shows the number of lines gained and the number of eyes over the study period. There is an increase of 1.5 lines of visual acuity at 6 weeks and 2.1 lines at 3 months. In all cases the visual field testing has improved. Average lines of gained at 3 months is 2 lines.

The present invention confronts the problem of to improve visual acuity and visual fields in patients with nerve damage, and in particular with optic nerve damage due to glaucoma inflammation/ischaemia or trauma.

It has been found by the inventor that significant improvements in the visual acuity (using the EDTRS electronic chart) and in signs and symptoms of these conditions can be achieved using high doses of EPA, and preferably of EPA and DHA, in the indicated ratio and dosage amounts. The therapy is effective even for patients who are non-responsive or poorly responsive to other therapies. The therapy of the invention is particularly suitable for oral administration. The use of EPA and DHA in the indicated ratios and dosage amounts also avoids the side effects experienced with the known treatments (e.g., steroids).

In some embodiments, the EPA and DHA are for use together with a further therapeutic agent for simultaneous, sequential or separate administration. Preferably the further therapeutic agent is a steroid and/or immunosuppressive drug and/or other nutritional supplement.

The administration of the compositions and kits of parts described herein can be used to treat cranial neuropathies, scleritis, thyroid eye disease, chronic uveitis, vernal/atopic keratoconjunctivitis, conjunctival and corneal wounds, and other body conditions due to inflammation and damaged nerves. High doses omega 3 fatty acid supplementation may represent a significant therapeutic option for such patients.

Thus, in accordance with a first aspect of the present invention, there is provided a method of administering a composition comprising at least 3 g of omega 3 fatty acids, and more preferably 5 g of omega 3 fatty acids.

In a preferred embodiment of the first aspect of the invention, the method includes administering a composition comprising from 5 g to 15 g of omega 3 fatty acids.

An omega-3 fatty acid is an unsaturated fatty acid containing a final carbon-carbon double bond as the third bond from the alkyl end of the molecule (i.e. the end that is remote from the carboxylic acid group). Examples of omega-3 fatty acids are indicated in Table 1.

TABLE 1

| OMEGA-3 FATTY ACIDS |
|---|
| Eicosatetraenoic acid (ETA) 20:4 (n-3) a//-c/'s-8,11,14,17-eicosatetraenoic acid |
| 304 Eicosatrienoic acid (ETE) 20:3 (n-3) all-cis-11,14,17-eicosatrienoic acid 306 |
| Stearidonic acid (SDA) 18:4 (n-3) a//-c/s-6,9,12,15-octadecatetraenoic acid 276 |
| Linolenic acid (ALA) 18:3 (n-3) a//-c/'s-9,12,15-octadecatrienoic acid 278 |
| Hexadecatrienoic acid (HTA) 16:3 (n-3) a//-cs-7,10,13-hexadecatrienoic acid 250 |

In a preferred embodiment of the first aspect of the invention, the omega 3 fatty acid included in the composition to be administered is selected from the list consisting of: eicosapentaenoic acid (EPA), docosahexaenoic acid (DHA), alpha liniolenic acid (ALA), stearidonic acid (SA), eicosatetraenoic acid (ETA), or any combination thereof. In a preferred embodiment of the first aspect of the invention, the omega 3 fatty acid is eicosapentaenoic acid (EPA). As is shown in example 1, a minimum of 3.000 mg (3.0 g), preferably 3.400 mg (3.4 g) of EPA is required to observe clinically useful outcomes.

In a further preferred embodiment of the first aspect of the invention, the omega 3 fatty acids included in the composition to be administered are a combination of eicosapentaenoic acid (EPA) and docosahexaenoic acid (DHA), or any of their salts, ester, solvates, prodrugs, derivatives or analogs of EPA and DHA, or any combination thereof. In a still further preferred embodiment of the first aspect of the invention, eicosapentaenoic acid (EPA) and docosahexaenoic acid (DHA) are use in a mass ratio from 1:1 to 5:1, preferably is in the range of from 1:1 to 4:1, more preferably 1:1 to 3:1, still more preferably 1.5:1 to 2.5:1, yet more preferably 2.1:1 to 2.4:1, most preferably in the range of from 2.1:1 to 2.2:1. Still more preferably, the eicosapentaenoic acid (EPA) and docosahexaenoic acid (DHA) are in a mass ratio of about 2:1.

As defined in the present invention, eicosapentaenoic acid (EPA or also icosapentaenoic acid), CAS Registry Number: 10417-94-4, IUPAC name (5Z,8Z, 11Z,14Z,17Z)-5,8,11,14, 17-icosapentaenoic acid is an omega-3 fatty acid. In physiological literature, it is given the name 20:5(n-3). It also has the trivial name timnodonic acid. In chemical structure, EPA is a carboxylic acid with a 20-carbon chain and five cis double bonds; the first double bond is located at the third carbon from the omega end. Is a compound of formula (I): or any of their salts, ester, solvates, prodrugs, derivatives or analogs thereof.

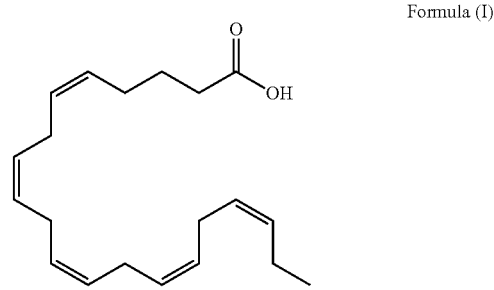 [SMILES: CC/C=C\C/C=C\C/C=C\C/C=C\C/C=C\CCCC(=O)O]

Formula (I)

EPA is a polyunsaturated fatty acid (PUFA) that acts as a precursor for prostaglandin-3 (which inhibits platelet aggregation), thromboxane-3, and leukotriene-5 groups (all eicosanoids).

As defined in the present invention, docosahexaenoic acid (DHA) is an omega-3 fatty acid that is a primary structural component of the human brain, cerebral cortex, skin, sperm, testicles and retina. It can be synthesized from alpha-linolenic acid or obtained directly from maternal milk or fish oil. DHA's structure is a carboxylic acid (~oic acid) with a 22-carbon chain (docosa—is Greek for 22) and six (Greek "hexa") cis double bonds (-en~);[2] the first double bond is located at the third carbon from the omega end. Its trivial name is cervonic acid, its systematic name is a//-c/'s-docosa-4,7,10, 13, 16, 19-hexa-enoic acid, and its shorthand name is 22:6(n-3) in the nomenclature of fatty acids. CAS Registry Number: 621 7-54-5, IUPAC name (4Z,7Z,10Z, 13Z,16Z, 19Z)-docosa-4,7,10, 13, 1 6, 1 9-hexaenoic acid; Doconexent is a compound of formula (II): their salts, ester, solvates, prodrugs, derivatives or analogs thereof.

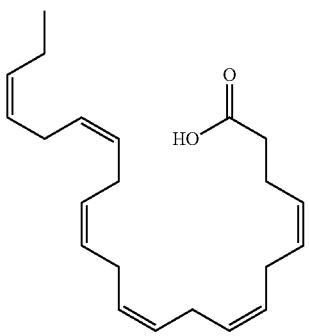

Formula (II)

As used herein, the term "derivative" includes both pharmaceutically acceptable compounds, i.e., derivatives of the compound of formula (I) or (II) which can be used in the preparation of a medicament, such as derivatives pharmaceutically unacceptable, as these may be useful in the preparation of derivatives pharmaceutically acceptable or the preparation of food compositions.

Also within the scope of this invention are prodrugs of the compounds of formula (I) or (II). The term "prodrug" as used herein includes any compound derived from a compound of formula (I) or (II), for example, esters, including carboxylic acid esters, amino acid esters, phosphate esters, sulphonate esters of metal salts, etc. carbamates, amides, etc., that, when administered to an individual is capable of providing, directly or indirectly, said compound of formula (I) or (II) in said individual. Advantageously, said derivative is a compound that increases the bioavailability of the compound of formula (I) or (II) when administered to an individual or enhancing the release of the compound of formula (I) in a biological compartment. The nature of said derivative is not critical provided it can be administered to an individual and provides the compound of formula (I) or (II) in a biological compartment of an individual. The preparation of said prodrug may be performed by conventional methods known to those skilled in the art.

In some embodiments, the EPA and/or DHA to be administered are in the form of a salt. Suitable salts include those formed with organic or inorganic bases. Pharmaceutically acceptable base salts include, but are not limited to, ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl- propylamine, or a mono-, di- or trihydroxy lower alkylamine, for example mono-, di- or triethanolamine.

In other embodiments, the EPA and/or DHA to be administered is/are in the form of an ester. Ester groups include those formed from the terminal carboxylic acid moiety of the omega-3 fatty acid and an alcohol, such as a C1-12 alkyl ester, formed by reaction of the omega-3 fatty acid with an alcohol having from 1 to 12 carbons, preferably a Ci-6 alkyl ester formed by reaction of the omega-3 fatty acid with an alcohol having from 1 to 6 carbons, for example a methyl, ethyl, n-propyl, /sopropyl, butyl, pentyl, or hexyl ester, formed by reaction of the omega-3 fatty acid with methanol, ethanol, n-propanol, /so-propanol, butanol, pentanol or hexanol. Preferably, the ester is an ethyl ester or a methyl ester, more preferably an ethyl ester.

In one preferred embodiment the EPA or salt or ester thereof to be administered comprises EPA and/or EPA ethyl ester, and the DHA or salt or ester thereof to be administered comprises DHA and/or DHA ethyl ester. More preferably, a combination of eicosapentaenoic acid and docosahexaenoic acid is used (i.e. the free acids of EPA and DHA are used, rather than salts or esters).

In a still further preferred embodiment of the first aspect of the invention, said composition to be administered is a pharmaceutical composition which optionally comprises an acceptable pharmaceutical carrier and/or additional active ingredients. More preferably, the pharmaceutical composition to be administered comprises at least 50% weight omega 3 fatty acids. Preferably, the composition to be administered comprises at least 30 weight % omega-3 fatty acid, more preferably at least 40 weight % of omega-3 fatty acid, still more preferably at least 50 weight % omega-3 fatty acid. Preferably, the composition to be administered comprises at least 30 weight %, more preferably at least 40 weight %, still more preferably at least 50 weight % of eicosapentaenoic acid. More preferably, the composition to be administered comprises at least 40 weight % of a combination of eicosapentaenoic acid and docosahexaenoic acid in a weight ratio of from 1:1 to 4:1, optionally in liquid form, more preferably at least 50 weight % of a combination of eicosapentaenoic acid and docosahexaenoic acid in a weight ratio of from 1:1 to 4:1, optionally in liquid form. In one particularly preferred embodiment, the composition to be administered comprises about 60 weight % of a combination of eicosapentaenoic acid and docosahexaenoic acid in a weight ratio of about 2:1, optionally in liquid form.

In another preferred embodiment, the composition to be administered is an oral dosage form. More preferably the oral dosage form is selected from the group comprising tablets, capsules, caplets, slurries, sachets, suspensions, chewing gum, and powder formulation that may be dissolved in a liquid. In a still more preferably embodiment, the oral dosage form is a suspension. In another still more preferably embodiment, the oral dosage form is a powder.

In another preferred embodiment, the composition to be administered is a food composition or a health food supplement. Preferably, the composition to be administered comprises at least 30 weight % omega-3 fatty acid, more preferably at least 40 weight % of omega-3 fatty acid, still more preferably at least 50 weight % of omega-3 fatty acid. Preferably, the composition to be administered comprises at least 30 weight %, more preferably at least 40 weight %, still more preferably at least 50 weight % of eicosapentaenoic acid. More preferably the composition to be administered comprises at least 40 weight % of a combination of eicosapentaenoic acid and docosahexaenoic acid in a weight ratio of from 1:1 to 4:1, optionally in liquid form, more preferably at least 50 weight % of a combination of eicosapentaenoic acid and docosahexaenoic acid in a weight ratio of from 1:1 to 4:1, optionally in liquid form. In one particularly preferred embodiment, the composition to be administered comprises about 60 weight % of a combination of eicosapentaenoic acid and docosahexaenoic acid in a weight ratio of about 2:1, optionally in liquid form.

Preferred food compositions are selected, but not limited, from: a beverage, infused food, milk, yogurt, cheese, fermented milk, flavored milk drink, soybean milk, precooked cereals, bread, cake, butter, margarine, sauces, frying oils, vegetable oils, corn oil, olive oil, soybean oil, palm oil, sunflower oil, cottonseed oil, condiments, salad dressings, fruit juices, syrups, desserts, icings and fillings, soft frozen products, confections, chewing gum and intermediate food.

The omega fatty acids EPA and DHA or salts or esters thereof to be administered may be administered simultaneously, sequentially or separately. Then a second aspect of the invention includes the administration of a kit of parts comprising eicosapentaenoic acid (EPA) and docosahexaenoic acid (DHA) in a mass ratio from 1:1 to 5:1, preferably is in the range of from 1:1 to 4:1, more preferably 1:1 to 3:1, still more preferably 1.5:1 to 2.5:1, yet more preferably 2.1:1 to 2.4:1, most preferably in the range of from 2.1:1 to 2.2:1. Still more preferably, the eicosapentaenoic acid (EPA) and docosahexaenoic acid (DHA) are in a mass ratio of about 2:1.

In a still further preferred embodiment of the second aspect of the invention, said kit of parts to be administered is a pharmaceutical kit of parts which optionally comprises an acceptable pharmaceutical carrier and/or additional active ingredients. More preferably, the additional active ingredient is a steroid, an anti-drug or a nutritional supplement. Other agents may be additional nutritional products such as polyphenols and other antioxidants. In one preferred embodiment, the further active ingredient is a steroid.

In other preferred embodiment, the composition to be administered is substantially free from antioxidants selected from the list consisting of vitamin E (including tocopherols and tocotrienols), epigallocatechin-3-gallate (EGCG), vitamin C, lutein and zeaxanthin. In one preferred embodiment, the composition to be administered is substantially free from anti-oxidants. In one preferred embodiment, the composition to be administered contains no anti-oxidants.

In another embodiment of the first aspect of the invention, said kit of parts to be administered is a food kit of parts. The kit of parts to be administered may comprise separate formulations of eicosapentaenoic acid (EPA) and docosahexaenoic acid (DHA). The separate formulations of EPA and DHA may be administered sequentially, separately and/or simultaneously (optionally repeatedly). Thus, the two active ingredients can be administered either as a part of the same composition (food or pharmaceutical composition) or in separate compositions (food or pharmaceutical compositions). EPA can be administered prior to, at the same time as, or subsequent to administration of DHA, or in some combination thereof.

The term "kit of parts", "combined preparation" or also called "juxtaposition" herein, means that the components of the combined preparation need not be present as a union (the components in the combination did not enter into direct interaction with each other), for example in a composition, to be available for use separately or sequentially. Thus, the term "juxtaposed" means that is not necessarily true combination, in view of the physical separation of the components.

A third aspect of the inventions refers to the composition or the kit of parts to be administered for use in therapy or for use as a medicament or medicine.

The term "medicine" or "medicament" as used herein refers to any substance used for prevention, diagnosis, alleviation, treatment or cure of disease in man and/or animals.

As shown in examples of the present invention, the use of EPA and DHA in the indicated ratios and dosages, provides a particularly effective therapy for those conditions and avoids the side effects of steroids if indicated. Currently there is no therapy to improve vision and field test in patients with optic nerve damage due to glaucoma.

A fourth aspect of the invention refers to the composition or the kit of parts to be administered for its use in the treatment, amelioration or prevention of diseases which involve damage to the nervous system, as the peripheral nervous system neuropathy and glaucoma.

In a preferred embodiment of the fourth aspect of the invention, the diseases which involve damage to the nervous system is selected from the group consisting of 2nd cranial (optic) nerve neuropathy, 3rd cranial nerve neuropathy (occulomotor), 4th cranial nerve neuropathy (trochlear), 6th cranial nerve neuropathy (abducent), 7th nerve neuropathy (facial), optic nerve damage, and other eye pathologies due to inflammation.

Optic nerve damage can occur mainly due to glaucoma, ischaemia, inflammation or trauma.

In a more preferred embodiment of the fourth aspect of the invention, the optic nerve damage is selected from the group consisting of optic nerve damage due to glaucoma, ischaemic optic neuropathy (ION), and optic neuritis, or any combination thereof. In another preferred embodiment of the fifth aspect of the invention, the eye pathology due to inflammation is selected from the group consisting of scleritis, thyroid eye disease, chronic uveitis, vernal and atopic keratoconjunctivitis, conjunctival and corneal wounds. A particular embodiment of the fourth aspect of the invention refers to the composition or the kit of parts to be administered for its use in the treatment, amelioration or prevention of glaucoma.

The precise dosage of the further active ingredient will vary with the dosing schedule, the oral potency of the particular agent chosen, the age, size, sex and condition of the subject, the nature and severity of the disorder to be treated, and other relevant medical and physical factors. Thus, a precise pharmaceutically effective amount cannot be specified in advance, but can be readily determined by the caregiver or clinician. An appropriate amount can be determined by routine experimentation from animal models and human clinical studies. For humans, an effective dose will be known or otherwise able to be determined by one of ordinary skill in the art.

The medicament of the invention may advantageously be administered in a single daily dose, or the total daily dosage may be administered in doses of two, three or four times daily. Preferably, the EPA and DHA, or a salt or an ester thereof is for administration once per day or twice per day.

In a more preferred embodiment, the pharmaceutical composition or kit of parts is to be administered one or more times a day; for example, 1, 2, 3 or 4 times a day, in a typical total daily amount to be above 5 g per day of omega 3 fatty acids, more preferably to be above 5 g per day of eicosapentaenoic acid (EPA) and docosahexaenoic acid (DHA), and more preferably comprised between 5 g to 15 g per day. Preferably, the combined dosage is from 7.5 g to 10 g per day. In a more preferred embodiment, the pharmaceutical composition or kit of parts can be administered in a dose wherein the combined EPA and DHA is such that the arachidonic acid/eicosapentaenoic acid mass ratio in the blood is in the range of 0.8 to 3 preferably between 1 to 1.5.

A fifth aspect of the invention refers to the use of the food composition to be administered for the treatment, amelioration or prevention of diseases which involve damage to the nervous system, as the peripheral nervous system neuropathy and glaucoma.

In a preferred embodiment of the fifth aspect of the invention, the diseases which involve damage to the nervous system is selected from the group consisting of 2nd cranial (optic) nerve neuropathy, 3rd cranial nerve neuropathy (occulomotor), 4th cranial nerve neuropathy (trochlear), 6th cranial nerve neuropathy (abducent), 7th nerve neuropathy (facial), optic nerve damage, and other eye pathologies due to inflammation.

Optic nerve damage can occur mainly due to glaucoma, ischaemia, inflammation or trauma.

In a more preferred embodiment of the fifth aspect of the invention, the optic nerve damage is selected from the group consisting of optic nerve damage due to glaucoma, ischaemic optic neuropathy (ION), and optic neuritis, or any combination thereof. In another preferred embodiment of the fifth aspect of the invention, the eye pathology due to inflammation is selected from the group consisting of scleritis, thyroid eye disease, chronic uveitis, keratoconjunctivitis, conjunctival and corneal wounds. A particular embodiment of the fifth aspect of the invention refers to the administration of the food composition of the invention for the treatment, amelioration or prevention of glaucoma. More preferably, the composition or the kit of parts is administered for use in the treatment of a patient population that is poorly responsive or nonresponsive to steroids.

In a more preferred embodiment, the food composition can be administered one or more times a day, for example, 1, 2, 3 or 4 times a day, in a typical total daily amount to be above 5 g per day of omega 3 fatty acids, more preferably to be above 5 g per day of eicosapentaenoic acid (EPA) and docosahexaenoic acid (DHA), and more preferably comprised between 5g to 15 g per day. Preferably, the combined dosage is from 7.5 g to 10 g per day. In a more preferred embodiment, the pharmaceutical composition or kit of parts can be administered in a dose wherein the combined EPA and DHA is such that the arachidonic acid/ eicosapentaenoic acid mass ratio in the blood is in the range of 0.8 to 3 preferably between 1 to 1.5.

The therapy of the invention has been shown to be particularly effective for treatment of the indicated conditions. Administrations of EPA and DHA in the doses and ratios used have been shown to result in improved vision in patient and/or improved symptoms. In patients with optic nerve damage due to glaucoma, the inventor has seen improvement in visual acuity and in the field test. This suggests that high doses EPA and DHA in the doses and ratios used can be beneficial to provide neuroprotection for the optic nerve.

It is believed that the methods disclosed herein remove neuroinflammation and provide neuroregeneration of the cranial nerve axons. Such methods also act as a potent anti-inflammatory agent for the brain and orbit.

In a preferred embodiment, the condition is optic neuropathy due to glaucoma/inflammation/ischaemia/toxicity or surgery. The therapy of the invention has been shown to improve the visual acuity and the field test, probably due to neuroregeneration and removal of neuroinflammation.

In a preferred embodiment, the condition is due to 3/4/6 cranial nerve neuropathy causing diplopia. The therapy of the invention has been shown to provide complete resolution of the neuropathy. This is likely due to neuroregeneration and removal of neuroinflammation.

In a preferred embodiment, the condition is facial nerve neuropathy. The therapy of the invention has been shown to provide complete resolution of the neuropathy.

In a preferred embodiment, the condition is any of the cranial nerve neuropathies. The present invention may provide complete resolution due to neuroregeneration and removal of neuroinflammation.

In a preferred embodiment, the condition is scleritis. The methods disclosed herein have been shown to improve the symptoms and signs of the patients. This is probably due to resolution of neuroinflammation.

In a preferred embodiment, the condition is due to inflammation in or around the eye e.g. thyroid eye disease, chronic uveitis, vernal or atopic keratoconjunctivitis. The methods disclosed herein have been shown to improve the symptoms and signs of these patients. This is probably due to resolution of neuroinflammation.

In a preferred embodiment, the condition is due to corneal or conjunctival wound. The composition of the invention has been shown to improve the symptoms and signs of these patients.

DEFINITIONS

As it used here, the terms "active ingredient", "active substance", "active pharmaceutical substance", "active principle" or "active pharmaceutical ingredient" means any component that potentially provides a pharmacological activity or another different effect in the diagnosis, cure, mitigation, treatment or prevention of a disease, or that affect the structure and function of the human body and of other animals. The term includes those components that promote a chemical change in the elaboration of the medicament and that are present in the same in a predicted modified form that provides the specific activity or the effect.

Either compositions or the kits of parts to be administered according to the methods disclosed herein can be formulated for administration in an animal and more preferably in a mammal, including humans, in a variety of forms known in the state of the art. Therefore, they can be included, but not limited to, sterile aqueous solution or in biological fluids, such as serum. The aqueous solutions could be buffered or not and they can contain other active or inactive ingredients as well. The additional components include salts to modulate ionic strength, preservatives, including but not limited to, antimicrobial agents, antioxidants, chelating agents and similar, and nutrients including glucose, dextrose, vitamins and minerals. Alternatively, the compositions to be administered may be prepared for its administration in solid form. Compositions can be combined with other various vehicles or inert excipients, including but not limited to: agglutinating agent such as microcrystalline cellulose, tragacanth, gelatin; excipients such as starch or lactose; dispersant agents such as alginic acid of maize starch; lubricants such as magnesium stearate; gliding agents such as colloidal silicon dioxide; sweetener such as sucrose or saccharine; or aromatic agents such as mint or methyl salicylate.

The term "medicament", as it is used in this report, makes reference to any substance used for prevention, diagnosis, relief, treatment or cure of diseases in humans and animals.

In the context of the present invention, the disease is a disease which involves damage to the nervous system.

Such compositions or combined preparations and/or its formulations may be administered in an animal, including a mammal and therefore humans, in a variety of forms, including but not limited to, intraperitoneal, intravenous, intramuscular, subcutaneous, intrathecal, intraventricular, oral, enteral, parenteral, intranasal or topic.

The dose to obtain an amount therapeutically effective depends on a variety of factors, such as for instance, age, sex, weight, tolerance of the mammal. In the sense used in this description, the term "amount therapeutically effective" refers to the amount of omega 3 fatty acids, preferably eicosapentaenoic acid (EPA), and more preferably a combination of eicosapentaenoic acid (EPA) and docosahexaenoic acid (DHA), that produce the desired effect and in general it is determined among other factors, by the intrinsic characteristics of the prodrug, derivatives or analogs and by the therapeutic effect to be obtained. The "adjuvant" and "vehicles pharmaceutically acceptable" that could be used in such compositions are well known vehicles in the field.

The term "pharmaceutically acceptable carrier" is intended to include formulation used to stabilize, solubilize and otherwise be mixed with active ingredients to be administered to living animals, including humans. This includes any and all solvents, dispersion media, coatings, antibacterial and antifungal agents, isotonic and absorption delaying agents, and the like, compatible with pharmaceutical administration. Except insofar as any conventional media or agent is incompatible with the active compound, such use in the compositions is contemplated.

The invention now will be described with respect to the following examples; however, the scope of the present invention is not intended to be limited thereby.

EXAMPLE 1

Method and Materials: A pilot study of 10 eyes with advanced optic nerve damage due to glaucoma. All eyes had reduced visual acuity and reduced field test. They were treated with omega 3 which consisted of purified ethyl esters rich in EPA (40 0mg) and DHA (200 mg) per gram for the liquid formulation. The dosage used in this pilot study was 15 ml to 20 ml of liquid formulation providing approximately 5.1 g to 6.8 g of EPA and 2.4 g to 3.2 g of DHA per day. The dosage was divided into two daily doses of 7.5 to 10 ml each. The dose was adjusted so that the blood AA/EPA ratio was within 1 to 1.5. The intraocular pressures an all eyes were well controlled with anti-glaucomatous drops.

Study 1 Results: The visual acuity was recorded using the EDTRS electronic chart at 6 weeks and 3 months. Visual field testing was also recorded with a field testing machine (Zeiss, Humphreys).

FIG. 1 shows the number of lines gained and the number of eyes over the study period. There is an increase of 1.5 lines of visual acuity at 6 weeks and 2.1 lines at 3 months. In all cases the visual field testing has improved. The use of prior art does not result in any therapeutic benefits to subjects with this ophthalmological conditions. In particular, the levels of the omega-3 fatty acid, eicosapentaenoic acid (EPA), in each of the prior art is far too low to have any therapeutic effect. It is this critical threshold of EPA required to induce a therapeutic effect that is the discovery of this patent application.

Figure 2:
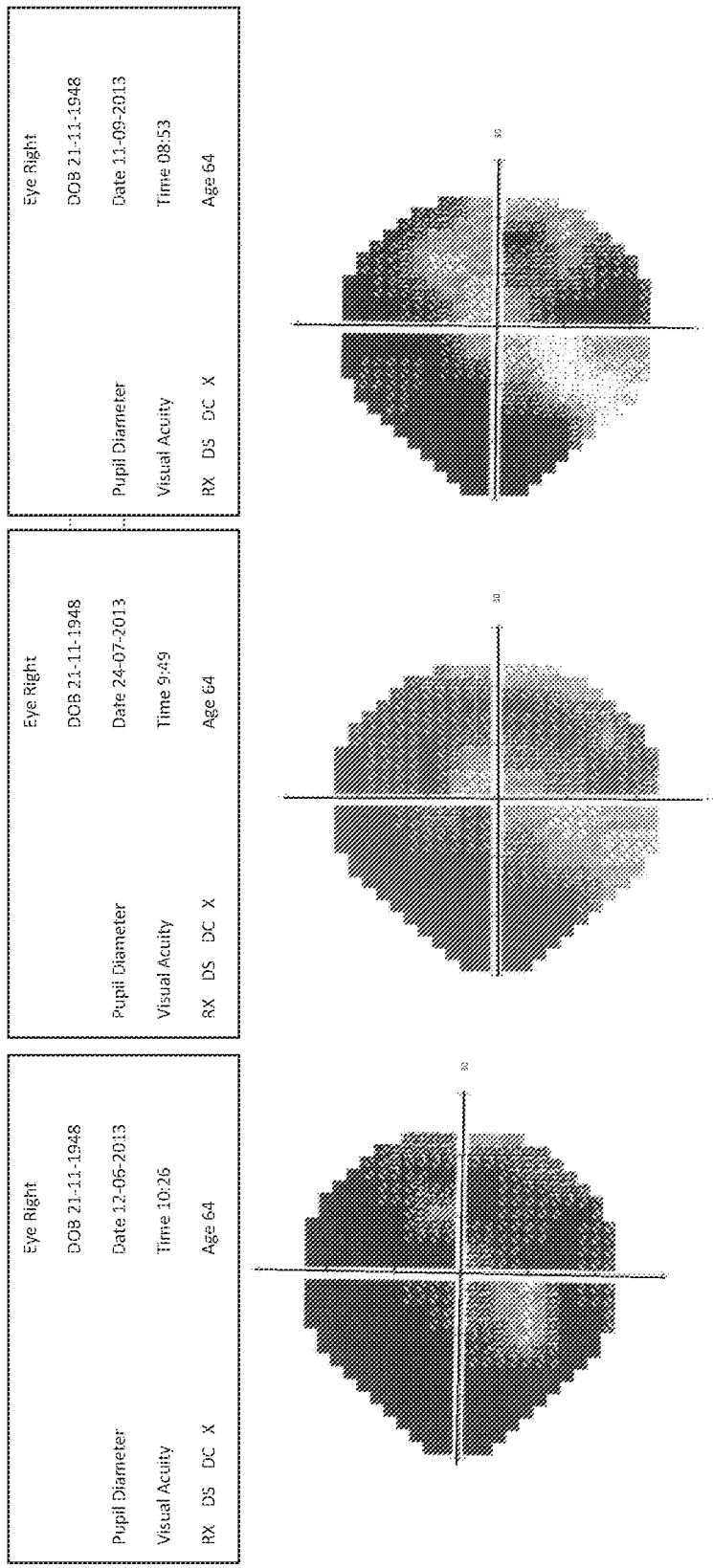
FIG. 2 shows an example of a 65 year old male with controlled intraocular pressures with anti-glaucoma drops. Field testing shows the improvement within 3 months of starting with 10 g per day of the invention. The visual acuity also improved by 3.5 lines within the 3 months. There is no previous art to show any improvement in vision acuity or any improvement in optic nerve function i.e. visual field.

FIG. 2 shows an example of a 65 years old male with controlled intraocular pressures with anti-glaucoma drops. Field testing shows the improvement within 3 months of starting with 10 g per day of the composition of the invention. The visual acuity also improved by 3.5 lines within the 3 months. There is no previous art to show any improvement in vision acuity or any improvement in optic nerve function i.e. visual field.

Figure 3A:
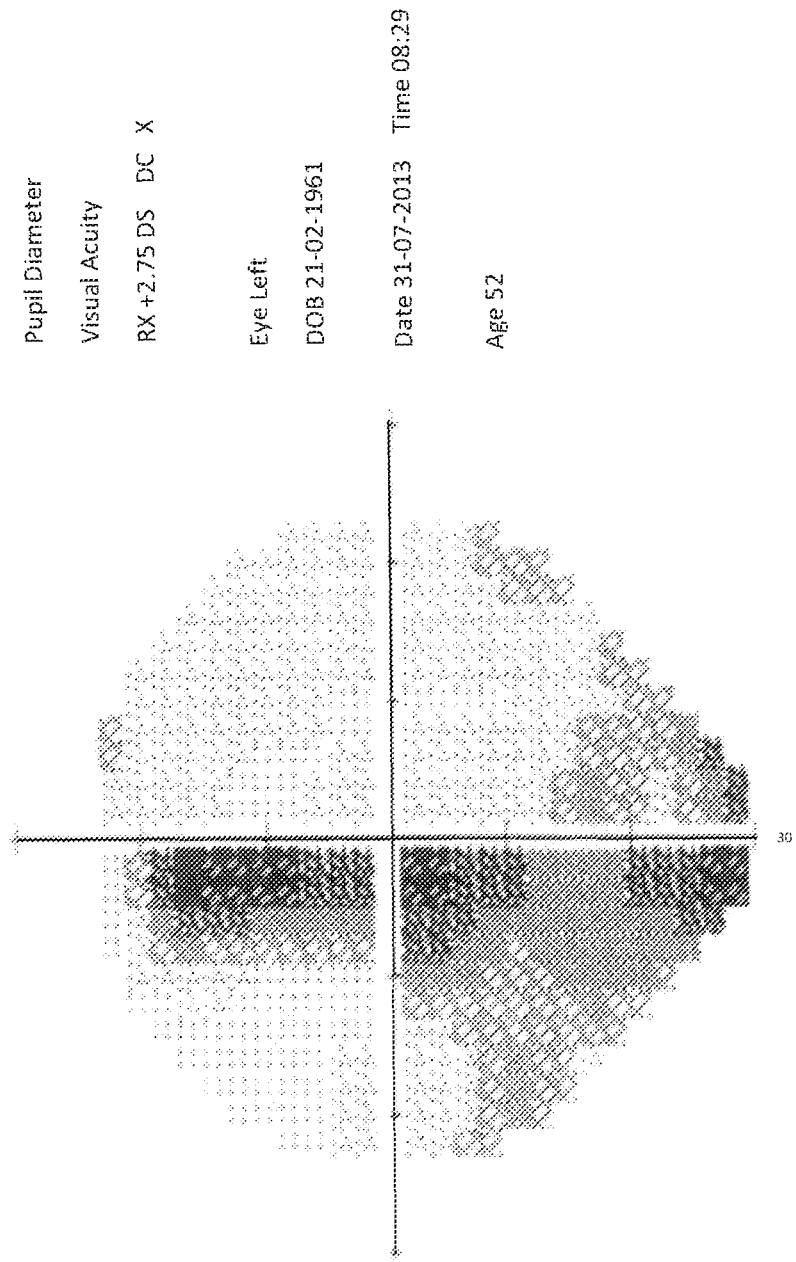
FIGS. 3A-3B show another example of a 53 year old man with advanced glaucoma. His intraocular pressures are controlled with anti-glaucomatous eye drops. His visual acuity in the left eye was 20/50 and has an advanced field loss as shown the field test. He was started on 8 g of the composition of the invention per day. At 2.4 months his gained 2 lines of vision and his field test improved as shown. There is no previous art to show any clinical improvement in vision or field test.
Figure 3B:
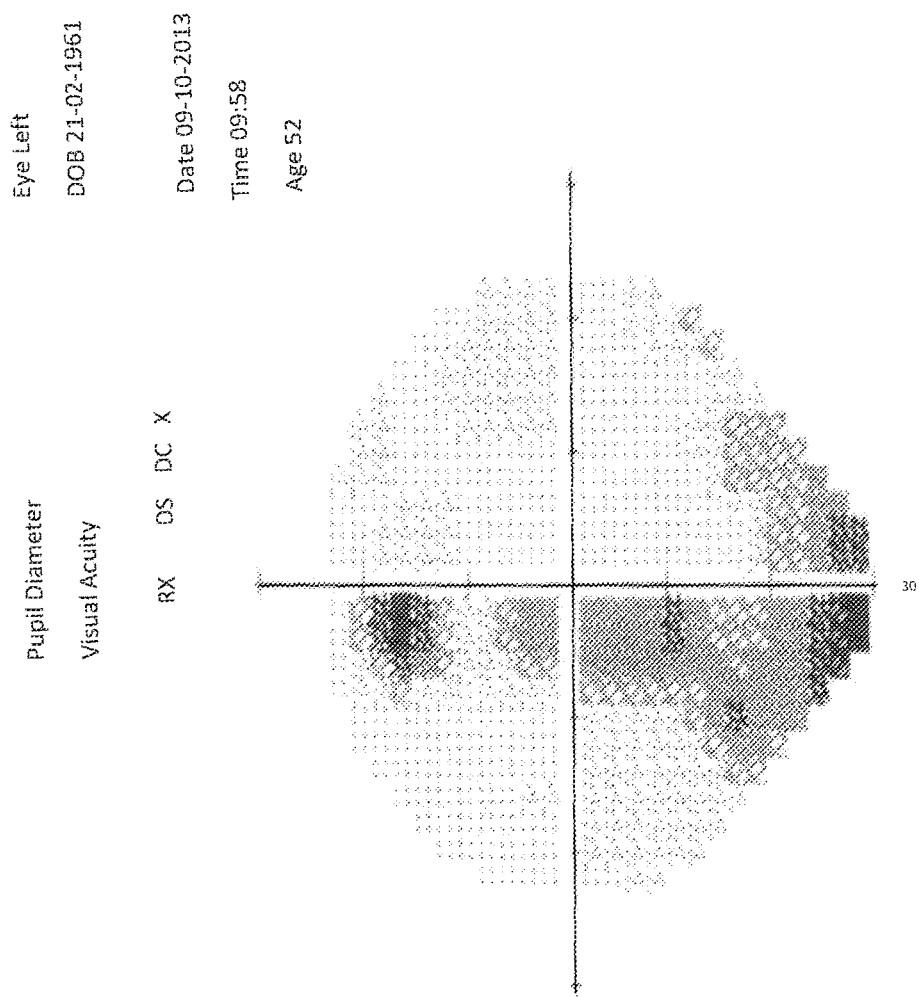

FIG. 3 shows another example of a 53 years old man with advanced glaucoma. His intraocular pressures are controlled with anti-glaucomatous eye drops. His visual acuity in the left eye was 20/50 and has an advanced field loss as shown the field test. He was started on 8g of the composition of the invention per day. At 2.4 months his gained 2 lines of vision and his field test improved as shown. There is no previous art to show any clinical improvement in vision or field test.

Conclusion of study 1: There are no current therapies to improve vision and field test in patients with glaucomatous optic nerve damage. From our study, our invention can be used to improve visual acuity and visual field in patients with optic nerve damage due to glaucoma. Since there is no existing treatment for the optic nerve damage due to glaucoma to stop progression of the disease, the positive clinical improvements obtained in this pilot study should be considered striking since 100% of the eyes had an increase in visual acuity and field testing. There is no previous art to show any improvement in vision or field test. This again indicates the discover in this patent application that a minimum of 3.000 mg, preferably 3.400 mg of EPA is required to observe clinically useful outcomes.

EXAMPLE 2

Method and Materials: A pilot study of 10 eyes with optic nerve damage due to ischaemia, inflammation and post trauma. These patients had a minimum of 6 months post optic nerve damage before starting on our treatment. They were treated with omega 3 which consisted of purified ethyl esters rich in EPA (400 mg) and DHA (200 mg) per gram for the liquid formulation. The dosage used in this pilot study was 15 ml to 20 ml of liquid formulation providing approximately 5.1 g to 6.8 g of EPA and 2.4 g to 3.2 g of DHA per day. The dosage was divided into two daily doses of 7.5 to 10 ml each. The dose was adjusted so that the blood AA EPA ratio was within 1 to 1.5.

Study 2 Results: The visual acuity was recorded using the EDTRS electronic chart at 6 weeks 3 months and 4.5 months.

FIG. 4 shows the number of lines gained and the number of eyes over the period of 4.5 months. There is an increase of 1.6 lines of visual acuity at 6 weeks, 2.4 lines at 3 months and 2.5 lines at 4.5 months.

There was also improved visual field testing in all the cases that were tested.

Figure 5A:
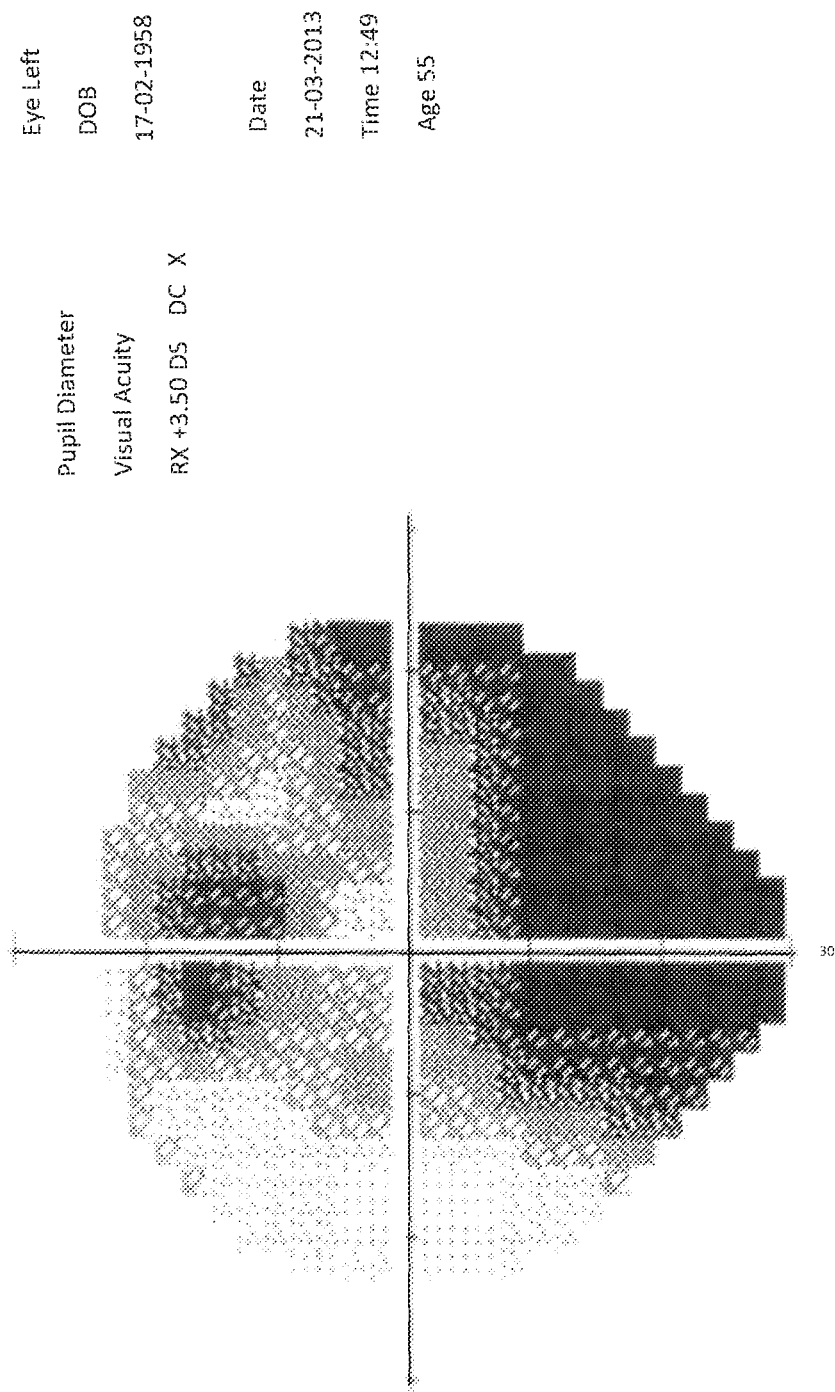
FIGS. 5A-5C show an example of a 55 year old man who had ischaemic optic neuropathy 6 months previous to presentation in the clinic. His visual acuity was 20/50. He was started on 10g/day of the composition according to the invention. 5 months following treatment his vision improved by 4 lines and the visual field test improved as shown.
Figure 5B:
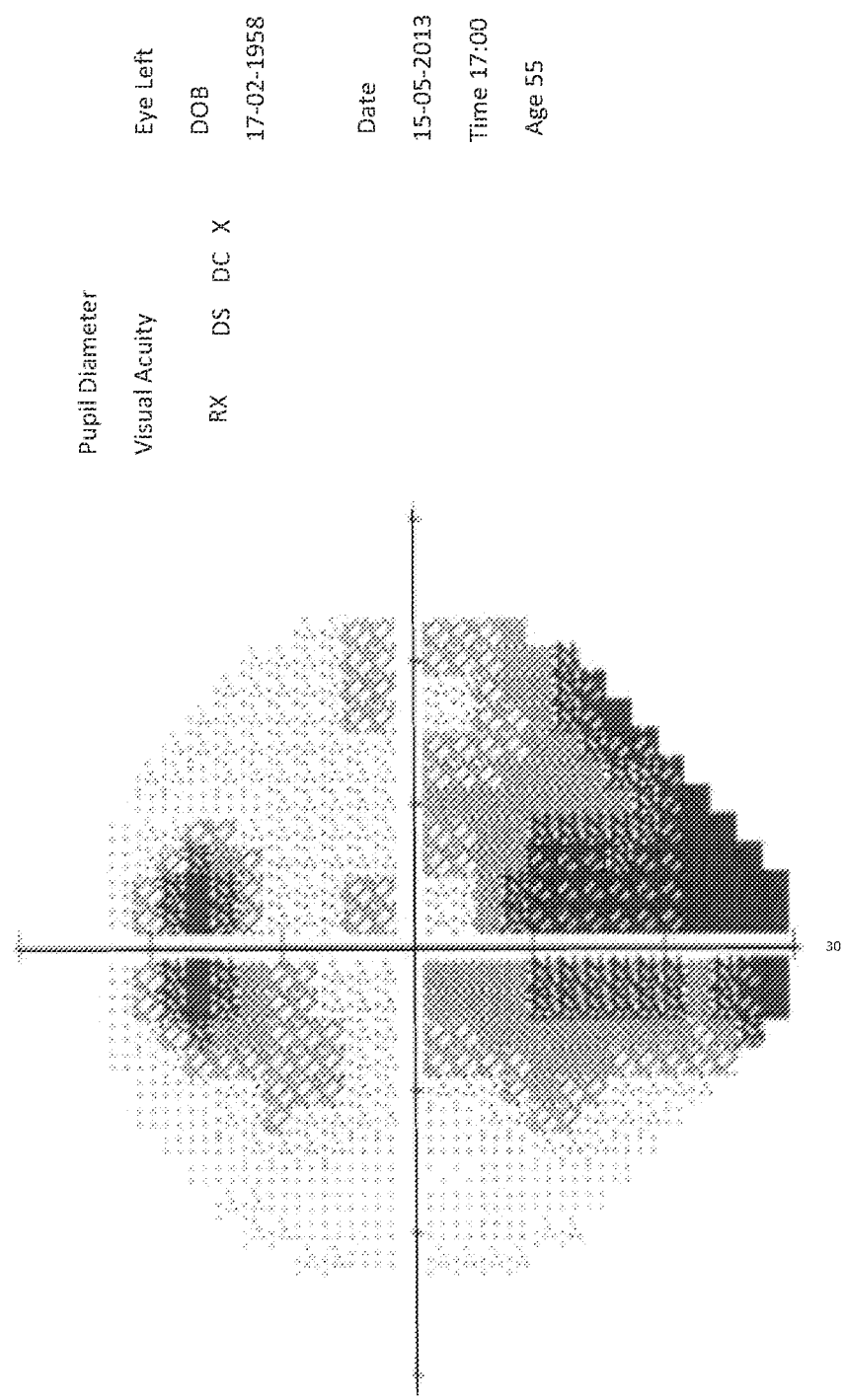
Figure 5C:
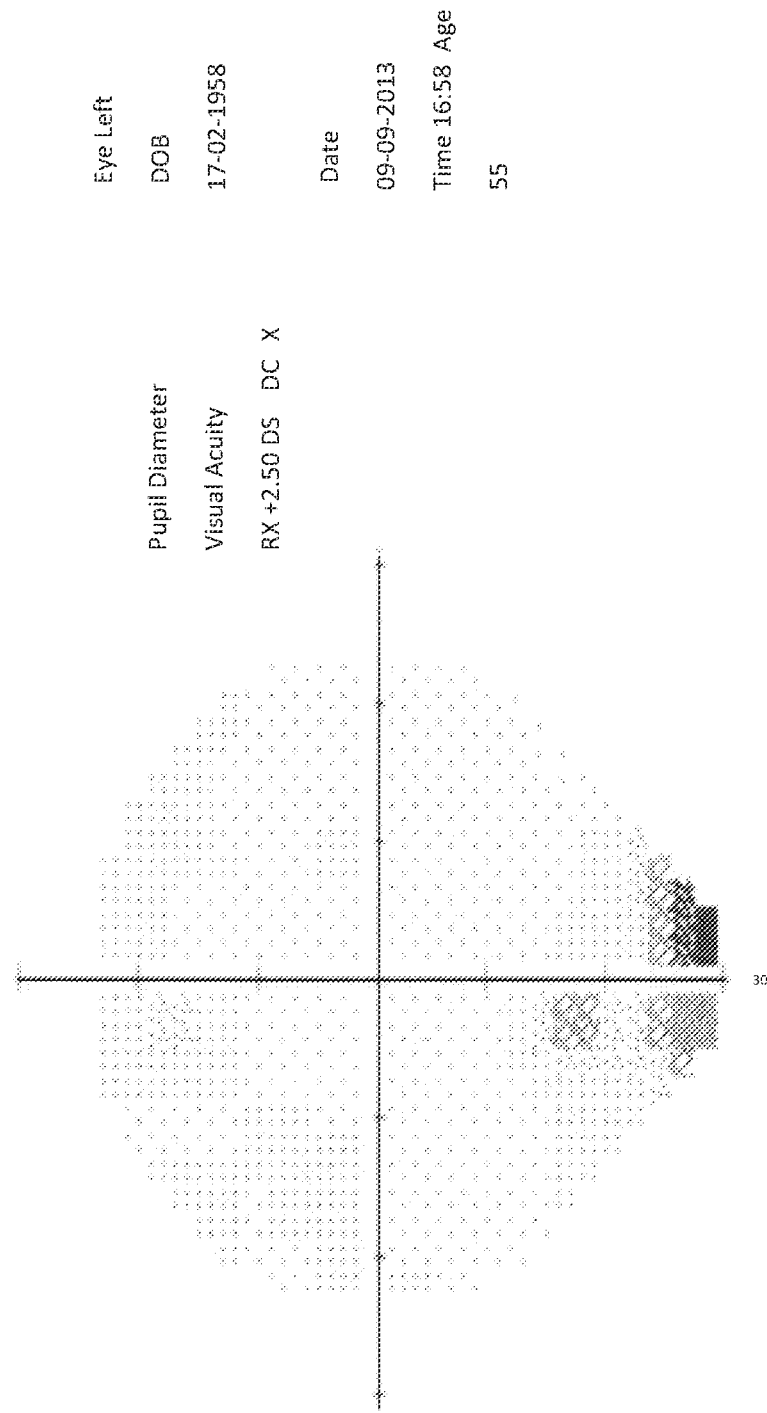

FIG. 5 shows an example of a 55 years old man who had ischaemic optic neuropathy 6 months previous to presentation in the clinic. His visual acuity was 20/50. He was started on 10g/day according to the invention. 5 months following treatment his vision improved by 4 lines and the visual field test improved as shown.

Figure 6B:
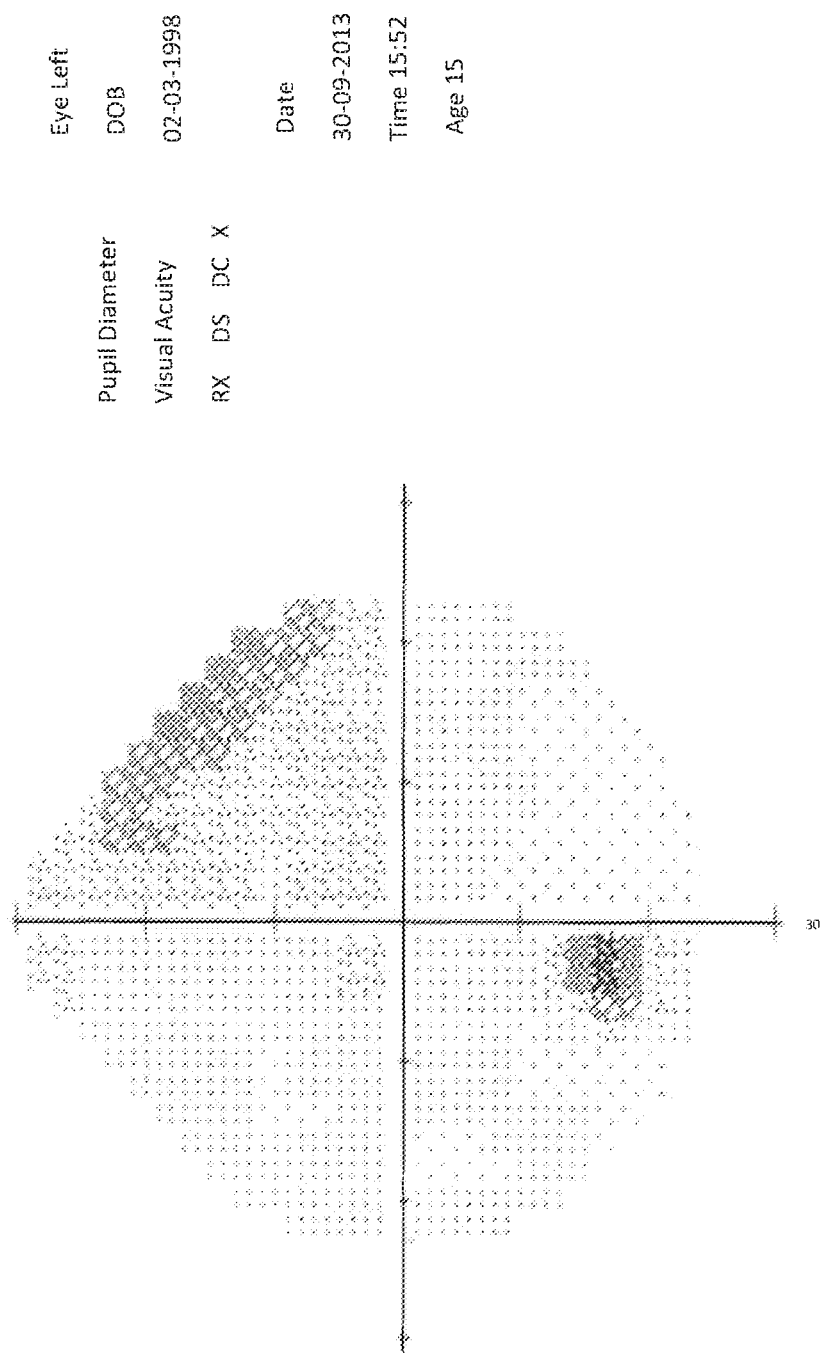
Figure 6C:
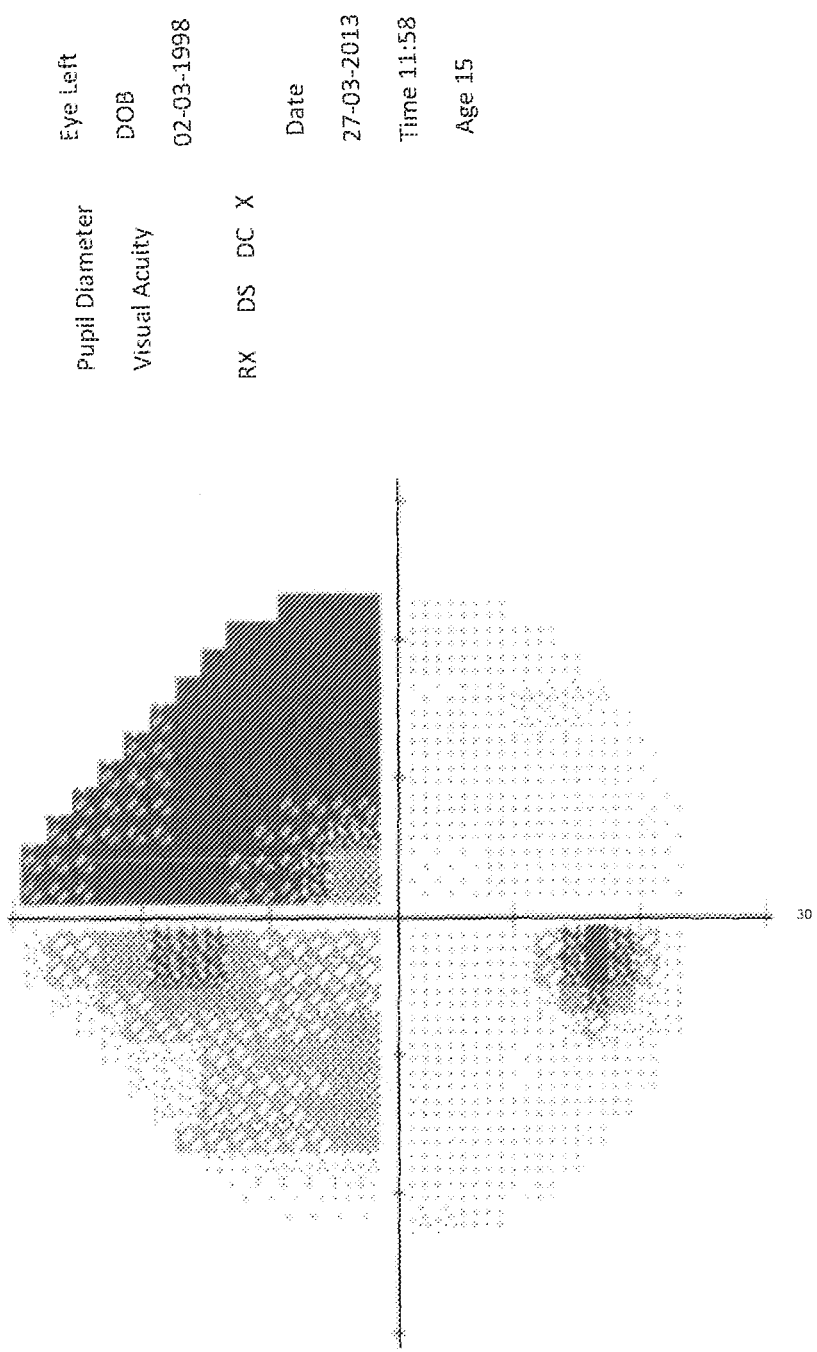

FIG. 6 shows an example of a 15 years old boy who presented 14 months following a road traffic accident. His visual acuity was 20/40 and had optic nerve damage as shown with the field test. He was started on 7.5g/day of the composition of the invention. 5.5 months following treatment his visual acuity improved by 2.5 lines and the field test has improved as shown.

Conclusion of study 2; The invention can be used to improve visual acuity and visual fields in patients with optic nerve damage due to inflammation/ischaemia or trauma. The use of prior art does not result in any therapeutic benefits to subjects with this ophthalmological conditions. In particular, the levels of the omega-3 fatty acid, eicosapentaenoic acid (EPA), in each of the prior art is far too low to have any therapeutic effect.

EXAMPLE 3

Two patients with scleritis who are only controlled with 10 mg of prednisolone had to stop due to the side effects of the steroid. In both cases, using the invention of 8 g per day of EPA and DHA were used to control their symptoms over at least 1 year follow up.

EXAMPLE 4

The invention was used in four patients with 4th cranial nerve neuropathy, three patients with 3rd nerve neuropathy, three patients with 6th nerve neuropathy and 2 patients with 7th cranial nerve neuropathy. The symptoms of the patients resolved within 2 to 3 months by using 7.5 g to 10 g per day of EPA and DHA and having a ratio of AA/EPA within 1 to 1.5.

EXAMPLE 5

The invention was used in 3 patients with moderate thyroid eye disease. The patients were controlled with 10 mg of prednisolone or with 7.5 g to 10 g of EPA and DHA and having a AA/EPA ratio between 1 to 1.5.

EXAMPLE 6

Three patients with more than 6 months of nonhealing corneal epithelial defects were treated with the invention. There was complete healing within 2 to 3 months with 7.5 g to 10 g of EPA and DHA and having a AA/EPA ratio between 1 to 1.5.

Having thus described the invention, what is desired to be protected by Letters Patent is presented in the subsequently appended claims.

What is claimed is:

1. A method for use in the treatment and amelioration of optic nerve damage comprising administering to a person a composition of at least 3 g of eicosapentaenoic acid and docosahexaenoic acid, in a mass ratio EPA:DHA from 2:1 to 5:1;

wherein the composition comprises at least 3 g of eicosapentaenoic acid.

2. A method for use in the treatment and amelioration of optic nerve damage due to glaucoma, ischemic optic neuropathy (ION), or optic neuritis, comprising administering to a person a composition comprising between 3 g and 15 g of eicosapentaenoic acid and docosahexaenoic acid, in a mass ratio EPA:DHA from 2:1 to 5:1;

wherein the composition comprises at least 3 g of eicosapentaenoic acid.

3. A method for use in the treatment and amelioration of glaucoma, comprising administering to a person a composition comprising between 3 g and 15 g of eicosapentaenoic acid and docosahexaenoic acid, in a mass ratio EPA:DHA from 2:1 to 5:1;

wherein the composition comprises at least 3 g of eicosapentaenoic acid.

4. The method according to claim 1, wherein the composition is a pharmaceutical composition.

5. The method according to claim 1, wherein the composition is a food composition.

6. The method according to claim 1, wherein the arachidonic acid/eicosapentaenoic acid mass ratio in the blood is in the range of 0.8 to 3.0, preferably from 1 to 1.5.

* * * * *